US010393884B2

(12) United States Patent
Larbi

(10) Patent No.: US 10,393,884 B2
(45) Date of Patent: Aug. 27, 2019

(54) SYSTEM AND METHOD FOR DETECTING THE WEARING BY A PATIENT OF A FOOT ULCER OFFLOADING APPARATUS

(71) Applicant: Creative Specific Software, Saint Raphael (FR)

(72) Inventor: Ramzi Larbi, Antibes (FR)

(73) Assignee: CREATIVE SPECIFIC SOFTWARE, Saint Raphael (FR)

(*) Notice: Subject to any disclaimer, the term of this patent is extended or adjusted under 35 U.S.C. 154(b) by 340 days.

(21) Appl. No.: 15/363,210

(22) Filed: Nov. 29, 2016

(65) Prior Publication Data
US 2017/0160400 A1 Jun. 8, 2017

(30) Foreign Application Priority Data
Dec. 7, 2015 (FR) .................................... 15 61949

(51) Int. Cl.
| | | |
|---|---|---|
| *G01S 19/47* | (2010.01) | |
| *H04W 4/029* | (2018.01) | |
| *A61F 5/01* | (2006.01) | |
| *A61F 13/06* | (2006.01) | |
| *G01P 13/00* | (2006.01) | |

(Continued)

(52) U.S. Cl.
CPC ............ *G01S 19/47* (2013.01); *A43B 3/0005* (2013.01); *A61B 5/1112* (2013.01); *A61B 5/445* (2013.01); *A61B 5/4833* (2013.01); *A61B 5/6807* (2013.01); *A61F 5/0111* (2013.01); *A61F 13/069* (2013.01); *G01P 13/00* (2013.01); *G01S 19/14* (2013.01); *G01S 19/24* (2013.01); *H04W 4/029* (2018.02); *A43B 7/147* (2013.01);

(Continued)

(58) Field of Classification Search
None
See application file for complete search history.

(56) References Cited

U.S. PATENT DOCUMENTS 9,005,141 B1 * 4/2015 Najafi .................. A61B 5/1116
600/595
9,198,803 B1 * 12/2015 London ............. A61F 13/00029
(Continued)

OTHER PUBLICATIONS

Written Opinion and Preliminary Search report (6 pages) dated Aug. 23, 2016 out of French priority Application No. 1561949.

*Primary Examiner* — Fekadeselassie Girma
(74) *Attorney, Agent, or Firm* — Brinks Gilson & Lione; John C. Freeman

(57) ABSTRACT

A system and a method for detecting the wearing by a patient of a foot ulcer offloading apparatus are described. The system includes an electronic geolocation device and a data processing equipment item linked to the electronic geolocation device via a communication network, the electronic geolocation device is suitable for being secured to the offloading apparatus and includes electrical power supply means, geolocation data acquisition means and means for transmitting geolocation data over the communication network to the data processing equipment item. The data transmission means is linked to the acquisition means and data processing equipment item is suitable, following the reception of geolocation data transmitted by the electronic geolocation device, for detecting a movement of the foot ulcer offloading apparatus and for deducing therefrom the wearing by the patient of said offloading apparatus.

12 Claims, 4 Drawing Sheets

(51) Int. Cl.
*G01S 19/14* (2010.01)
*G01S 19/24* (2010.01)
*A61B 5/11* (2006.01)
*A61B 5/00* (2006.01)
*A43B 3/00* (2006.01)
*H04W 84/18* (2009.01)
*A43B 7/14* (2006.01)

(52) U.S. Cl.
CPC ............ *A61B 5/0022* (2013.01); *A61F 5/0195* (2013.01); *H04W 84/18* (2013.01)

(56) References Cited

U.S. PATENT DOCUMENTS

| | | | |
|---|---|---|---|
| 9,311,789 B1* | 4/2016 | Gwin | G08C 19/00 |
| 9,943,432 B1* | 4/2018 | Butler | A43B 13/183 |
| 2004/0198382 A1* | 10/2004 | Wong | H04B 1/3827 |
| | | | 455/456.1 |
| 2008/0001735 A1* | 1/2008 | Tran | G06F 19/3418 |
| | | | 340/539.22 |
| 2009/0209830 A1 | 8/2009 | Nagle | |
| 2011/0013002 A1* | 1/2011 | Thompson | A61B 5/0059 |
| | | | 348/77 |
| 2011/0153197 A1 | 6/2011 | Song | |
| 2011/0153261 A1* | 6/2011 | Jang | A43B 3/0005 |
| | | | 702/141 |
| 2012/0184878 A1* | 7/2012 | Najafi | A61B 5/112 |
| | | | 600/592 |
| 2013/0267223 A1* | 10/2013 | Tajima | H04W 76/19 |
| | | | 455/423 |
| 2014/0000125 A1* | 1/2014 | Butler | A43B 13/386 |
| | | | 36/43 |
| 2014/0156038 A1* | 6/2014 | Poyhtari | G06F 19/3481 |
| | | | 700/91 |
| 2014/0335490 A1 | 11/2014 | Baarman | |
| 2015/0096204 A1* | 4/2015 | Case, Jr. | A43B 1/0036 |
| | | | 36/136 |
| 2016/0089572 A1* | 3/2016 | Liu | G06K 9/00342 |
| | | | 434/255 |
| 2016/0206242 A1* | 7/2016 | Esposito | A61B 5/1038 |
| 2016/0213552 A1* | 7/2016 | Lindsay | A61F 5/0111 |
| 2016/0361648 A1* | 12/2016 | Kim | A63F 13/426 |
| 2017/0273398 A1* | 9/2017 | Butler | A43B 7/143 |
| 2017/0296625 A1* | 10/2017 | Gardner | A61K 38/1825 |
| 2018/0151037 A1* | 5/2018 | Morgenthau | G08B 25/016 |
| 2018/0176977 A1* | 6/2018 | Liu | H04W 24/04 |
| 2018/0280696 A1* | 10/2018 | Slepian | A61B 5/6807 |

* cited by examiner

SYSTEM AND METHOD FOR DETECTING THE WEARING BY A PATIENT OF A FOOT ULCER OFFLOADING APPARATUS

This application claims priority to French patent application No. 1561949 filed on Dec. 7, 2015, the entire contents of which is incorporated herein by reference.

BACKGROUND

The present invention relates to a system, a computer program product and a method for detecting the wearing by a patient of a foot ulcer offloading apparatus.

The foot is a priority target in diabetes complications. In effect, foot ulcers in diabetics constitute a genuine public health problem because of the epidemiology of this disease, the severity of the complications, the cost to society and finally the precariousness of the population concerned. Now, the growing number of diabetic patients will have an effect on the complications of diabetes and more particularly on the occurrence of malum perforans pedis.

To solve the problem of the healing or prevention of the occurrence of foot ulcers among diabetic patients, it is known practice to use foot ulcer offloading apparatuses. The offloading of an ulcer can be defined as any measure aiming to eliminate the abnormal points of pressure exerted on the ulcer to facilitate the healing thereof or to prevent the recurrence thereof.

A foot ulcer offloading apparatus can for example take the form of a medical boot specially adapted to offload ulcers. The principle of such an offloading apparatus is to allow the patient to maintain independence with physical activity that is essential to the treatment of the arteriopathy and to the balance of the diabetes while avoiding excessive pressure on the ulcer. Offloading is the treatment which gives the best results in terms of healing rate and time. It reduces the risk of infection and of amputation. Nevertheless, to be effective, the offloading has to be done 24 hours a day, 7 days a week. Abandoning this treatment is therefore very risky and the failure of the patient to follow the medical offloading treatment must be detected as early as possible by the practitioner following the patient, in order to possibly adjust the therapeutic patient management strategy.

Now, such offloading apparatuses are generally impractical for use and relatively uncomfortable and/or unsightly. Because of this, a high number of patients do not observe the medical prescription of the permanent wearing of the offloading apparatus, and do not inform their practitioner of this failure to observe the treatment. One of the problems encountered by the practitioners is therefore that of the difficulty of quantifying the amount of time the patient wears the offloading apparatus.

To solve this problem, systems are known for detecting the wearing by a patient of a foot ulcer offloading apparatus. One such system is for example described in the document US 2009/0209830 A1. The detection system comprises an electronic device for example arranged in the sole of an ulcer offloading boot, and a data processing equipment item linked to the electronic device via a communication network. The electronic device comprises a pressure sensor and means for transmitting pressure measurement data, over the communication network to the data processing equipment item. Thus, the wearing or not of the offloading apparatus by the patient can be detected by the data processing equipment item, by comparing the measured pressure values to a predetermined threshold. If a measured pressure value is below the threshold that means that the patient is not wearing the offloading boot.

However, such a detection system exhibits low accuracy because of the method of detection by the comparison of measured pressure values, notably for pressure values that are established around the predetermined threshold. Furthermore, a detection system of this kind does not make it possible to determine the distance covered by the patient provided with his or her ulcer offloading apparatus, nor does it make it possible to accurately quantify the time during which the offloading apparatus is worn by the patient.

There is therefore a real need for a system and a method for detecting the wearing by a patient of a foot ulcer offloading apparatus that mitigates these defects, drawbacks and obstacles of the prior art, in particular for a simple and reliable system that exhibits an improved detection accuracy, while making it possible to determine the distance covered by the patient provided with the offloading apparatus as well as the time spent covering the distance.

SUMMARY

To resolve one or more of the drawbacks of the prior art, according to one aspect of the invention, a system for detecting the wearing by a patient of a foot ulcer offloading apparatus comprises an electronic geolocation device and a data processing equipment item linked to the electronic geolocation device via a communication network, the electronic geolocation device being suitable for being secured to the offloading apparatus and comprising electrical power supply means, geolocation data acquisition means and means for transmitting geolocation data over the communication network to the data processing equipment item, the data transmission means being linked to the acquisition means, the data processing equipment item being suitable, following the reception of geolocation data transmitted by the electronic geolocation device, for detecting a movement of the foot ulcer offloading apparatus and for deducing therefrom the wearing by the patient of said offloading apparatus.

By virtue of the presence in the electronic device of geolocation data acquisition means, the data received by the data processing equipment item are geolocation data, transmitted by the device, for example periodically. The detection of the wearing by the patient of the offloading apparatus is performed by the data processing equipment item, either by detection of a change of value between two consecutive values of the geolocation data received, or via the simple reception of the geolocation data. The accuracy of the detection is thus, in all cases, improved. Furthermore, since position data of the electronic device are received sequentially by the data processing equipment item, the detection system according to the invention advantageously makes it possible to determine the distance covered by the patient provided with the offloading apparatus, and indirectly determine the time spent covering that distance.

According to particular embodiments that can be used alone or in combination:

the electronic geolocation device further comprises a motion sensor linked to the geolocation data transmission means, the geolocation data transmission means being configured to transmit geolocation data to the data processing equipment item when a movement of the device is detected by the motion sensor;

the system further comprises a second electronic geolocation device suitable for being fixed directly to the body of the patient, the second geolocation device being linked to the data processing equipment item via the communication network and comprising second electrical power supply means, second geolocation data acquisition means and second means for transmitting geolocation data over the communication network to the data processing equipment item, the second data transmission means being linked to the second acquisition means;

the second electronic geolocation device further comprises a second motion sensor linked to the second geolocation data transmission means, the second geolocation data transmission means being configured to transmit geolocation data to the data processing equipment item when a movement of the device is detected by the second motion sensor;

at least one of the geolocation devices comprises a GPS tracking beacon triggered instantaneously on movement of the device;

the data processing equipment item is suitable, following the reception of the geolocation data transmitted by the electronic geolocation devices, for computing an offloading rate associated with the wearing by the patient of the foot ulcer offloading apparatus;

the system further comprises an electronic communication device suitable for being fixed directly to the body of the patient, the electronic communication device comprising electrical power supply means and a radiofrequency signal transceiver;

the electronic communication device further comprises a motion sensor linked to the radiofrequency signal transceiver, the transceiver being configured to transmit radiofrequency signals when a movement of the communication device is detected by the motion sensor;

the electronic geolocation device further comprises a programmable microcontroller linked to the data transmission means, and a radiofrequency signal transceiver linked to the programmable microcontroller, the microcontroller being programmed to transmit a geolocation data transmission command signal to the data transmission means, accompanied by a first notification if a radiofrequency link has been established between the transceiver and the electronic communication device; and to transmit a geolocation data transmission command signal to the data transmission means, accompanied by a second notification, different from the first notification, if no radiofrequency link has been established between the transceiver and the electronic communication device;

the data processing equipment item is suitable, following the reception of the geolocation data transmitted by the electronic geolocation device and of the first or the second notification, for computing an offloading rate associated with the wearing by the patient of the foot ulcer offloading apparatus;

the data processing equipment item comprises a server, the server comprising a processor and a memory linked to the processor, the memory storing an application, the application being suitable, when it is implemented by the processor, for detecting the movement of the foot ulcer offloading apparatus and for deducing therefrom the wearing by the patient of said offloading apparatus, following the reception of the geolocation data transmitted by the electronic geolocation device.

According to a second aspect of the invention, a method for detecting the wearing by a patient of a foot ulcer offloading apparatus is implemented by a detection system comprising an electronic geolocation device and a data processing equipment item linked to the electronic geolocation device via a communication network, the electronic geolocation device being secured to the offloading apparatus and comprising electrical power supply means, geolocation data acquisition means, and means for transmitting geolocation data over the communication network to the data processing equipment item, the data transmission means being linked to the acquisition means, the method comprising the following steps:

acquisition of geolocation data by the data acquisition means;

transmission of the acquired geolocation data over the communication network, to the data processing equipment item;

detection by the data processing equipment item, from the received geolocation data, of a movement of the foot ulcer offloading apparatus, and, consequently, of the wearing by the patient of said offloading apparatus.

According to one particular embodiment, the detection system further comprises a second electronic geolocation device fixed directly to the body of the patient, the second geolocation device being linked to the data processing equipment item via the communication network and comprising second electrical power supply means, second geolocation data acquisition means and second means for transmitting geolocation data over the communication network to the data processing equipment item, the method further comprising the following steps:

acquisition of geolocation data by the second data acquisition means;

transmission of the geolocation data acquired by the second acquisition means over the communication network, to the data processing equipment item;

computation, by the data processing equipment item, of an offloading rate associated with the wearing by the patient of the foot ulcer offloading apparatus, whether or not the data processing equipment item has detected the wearing by the patient of the foot ulcer offloading apparatus.

According to another particular embodiment, the detection system further comprises an electronic communication device fixed directly to the body of the patient, the electronic communication device comprising electrical power supply means and a radiofrequency signal transceiver, the electronic geolocation device further comprising a programmable microcontroller linked to the data transmission means, and a radiofrequency signal transceiver linked to the programmable microcontroller, the method further comprising the following steps:

determination, by the programmable microcontroller, as to whether a radiofrequency link has been established between the transceiver of the electronic geolocation device and the transceiver of the electronic communication device;

transmission, by the programmable microcontroller, of a geolocation data transmission command signal to the data transmission means, accompanied by a first notification if a radiofrequency link has been established between the electronic geolocation device and the electronic communication device; or by a second notification, different from the first notification, if no radiofrequency link has been established between the electronic geolocation device and the electronic communication device;

computation, by the data processing equipment item, of an offloading rate associated with the wearing by the patient of the foot ulcer offloading apparatus, whether or not the data processing equipment item has detected the wearing by the patient of the foot ulcer offloading apparatus;

and, in the step of transmission of the acquired geolocation data, said transmitted geolocation data are accompanied by the first or the second notification.

According to a third aspect of the invention, a computer program product that can be downloaded from a communication network and/or stored on a computer-readable medium and/or that can be executed by a processor comprises program instructions, said program instructions forming the application of the server of the data processing equipment item as described hereinabove, said program instructions being adapted to implement the steps of detection of a movement of the foot ulcer offloading apparatus, and, consequently, of the wearing by the patient of said offloading apparatus, of the method as described hereinabove when the program product is run on said sever.

Other advantages will also occur to those skilled in the art on reading the examples below, illustrated by the attached figures, given by way of illustration.

DETAILED DESCRIPTION

Figure 1:
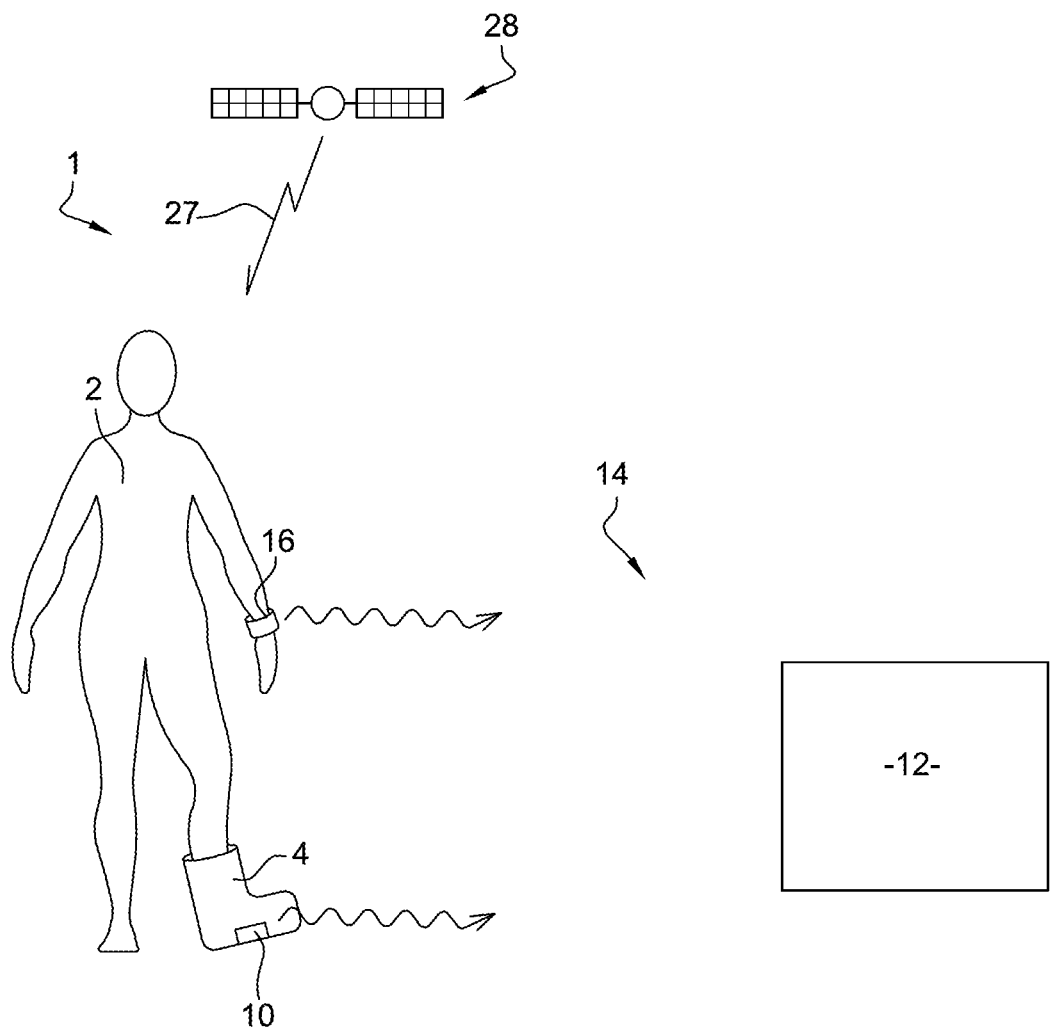
FIG. 1 is a schematic representation of a system for detecting the wearing by a patient of a foot ulcer offloading apparatus according to a first embodiment of the invention.

FIG. 1 shows a system 1 for detecting the wearing by a patient 2 of a foot ulcer offloading apparatus 4 according to a first embodiment of the invention. The offloading apparatus 4 can be an apparatus that is removable or non-removable. In the particular exemplary embodiment of FIG. 1, the offloading apparatus 4 is a medical boot specially adapted for the offloading of foot ulcers.

The detection system 1 comprises an electronic geolocation device 10 and a data processing equipment item 12 linked to the electronic device 10 via a communication network 14. In the particular exemplary embodiment of FIG. 1, the detection system 1 comprises a first electronic geolocation device 10 and a second electronic geolocation device 16.

The first electronic geolocation device 10 is suitable for being secured to the offloading apparatus 4. In the particular exemplary embodiment of FIG. 1, the first electronic geolocation device 10 is suitable for being arranged in a medical boot specially adapted for the offloading of foot ulcers, for example, but not exclusively, in a sole of this boot. In a variant that is not represented, the first electronic geolocation device 10 is suitable for being fixed to the medical boot.

Figure 2:
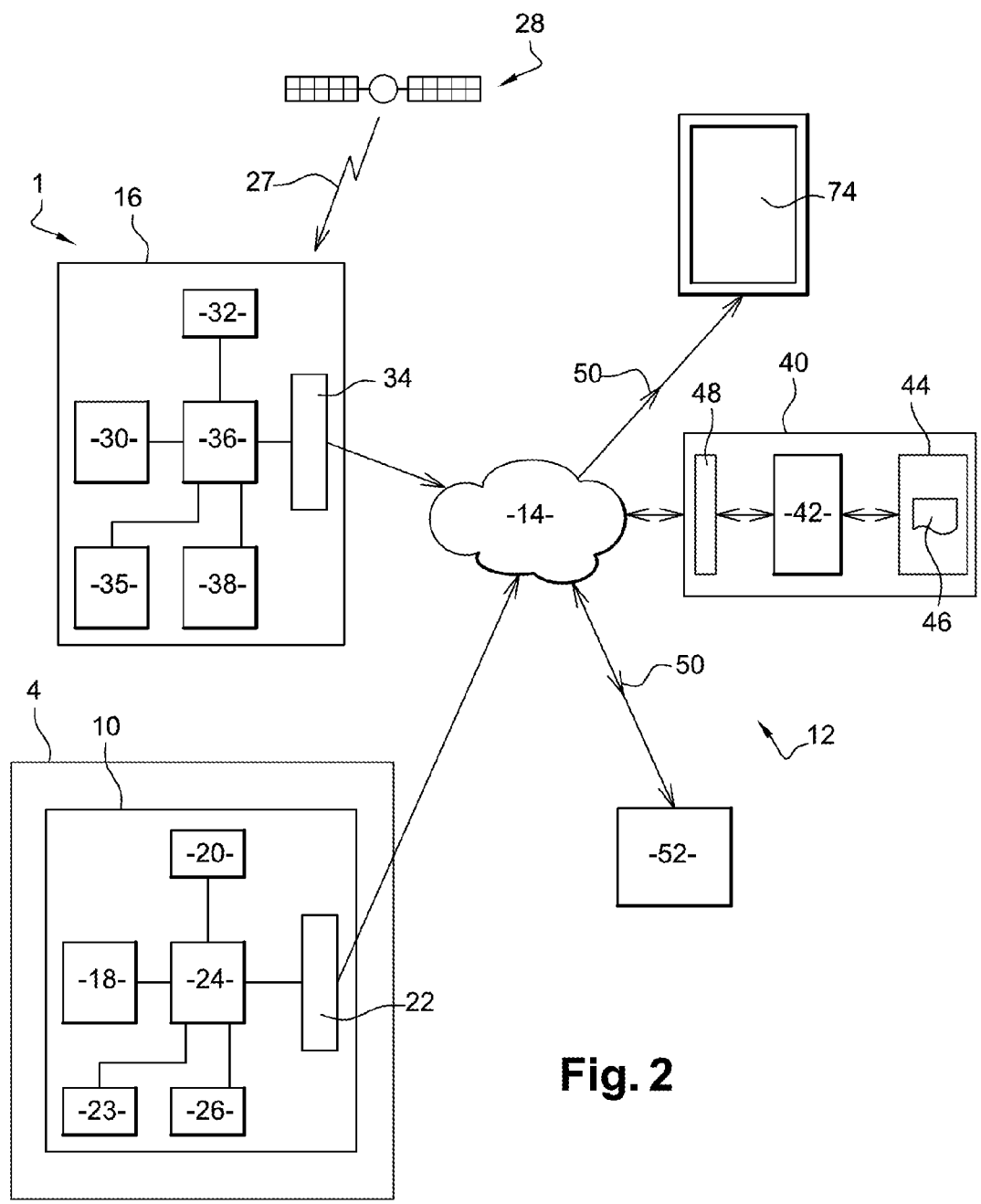
FIG. 2 represents the functional architecture of the detection system of FIG. 1.

As illustrated in FIG. 2, the first electronic geolocation device 10 comprises electrical power supply means 26, geolocation data acquisition means 20, and means 22 for transmitting geolocation data over the communication network 14, to the data processing equipment item 12. Preferably, as illustrated in FIG. 2, the first electronic geolocation device 10 further comprises a motion sensor 18, a pedometer 23 and a programmable microcontroller 24. In a variant, the programmable microcontroller 24 can be replaced by any type of computation and data processing means, such as, for example, a processor or a microprocessor.

The first electronic geolocation device 10 is for example formed by a protective casing within which is arranged a GPS (Global Positioning System) tracking beacon, preferably a GPS tracking beacon instantaneously triggered on movement of the device. In the particular case where the first geolocation device 10 is suitable for being arranged in the foot ulcer offloading apparatus 4, the first electronic geolocation device 10 has dimensions compatible with such an arrangement. The first electronic geolocation device 10 has, in particular, dimensions compatible with an arrangement within a medical boot, notably with an arrangement within a sole of such a boot, so as not to adversely affect the comfort of the patient wearing the boot, or hamper or prevent the walking movement of the patient. The thickness of the first electronic geolocation device 10 is for example of the order of a few millimeters.

The electrical power supply means 26 are for example able to supply a nominal electrical voltage substantially equal to 12 V. The electrical power supply means 26 are for example formed by a lithium battery, notably a lithium battery that can be recharged via a connector of micro-USB (Universal Serial Bus) type. The electrical power supply means 26 are for example able to supply the first electronic geolocation device 10 with electrical autonomy of the order of several months.

The geolocation data acquisition means 20 are configured to periodically trigger an acquisition of geolocation data. More specifically, in the preferential exemplary embodiment illustrated in FIG. 2, the programmable microcontroller 24 is programmed to periodically transmit a geolocation data acquisition command signal to the geolocation data acquisition means 20. The geolocation data acquisition means 20 comprise, for example, a GPS antenna, capable of receiving and acquiring GPS signals 27 transmitted by a GPS positioning satellite 28.

The means 22 for transmitting geolocation data over the communication network 14 are linked to the geolocation data acquisition means 20. The data transmission means 22 comprise, for example, an antenna conforming to the GSM (Global System for Mobile Communication) standard.

The motion sensor 18 is linked to the geolocation data transmission means 22. In the preferential exemplary embodiment illustrated in FIG. 2, the motion sensor 18 is connected to the programmable microcontroller 24; the latter being also connected to the geolocation data transmission means 22. The motion sensor 18 is, for example, a tri-axial linear accelerometer, capable of delivering a signal as soon as a non-zero acceleration value is measured. In a variant, the motion sensor 18 is an instantaneous speed sensor. In the preferential exemplary embodiment according to which the first electronic geolocation device 10 comprises a motion sensor 18, the geolocation data transmission means 22 are configured to transmit geolocation data to the data processing equipment item 12 when a movement of the device 10 is detected by the motion sensor 18. This preferential exemplary embodiment advantageously makes it possible to save electrical energy in the electrical power supply means 26, the transmission means 22 not transmitting data on a periodic basis but only if a movement of the device 10 has been detected by the motion sensor 18. Furthermore, this preferential exemplary embodiment also makes it possible to improve the accuracy of the detection. The time for acquisition and transmission of geolocation data by the first device 10, from the instant when a movement of the first device 10 is detected by the motion sensor 18, is preferably less than 1 second.

The pedometer 23 is connected to the programmable microcontroller 24 and is capable of supplying measurement data concerning the number of steps of the patient 2.

The programmable microcontroller 24 is linked to the motion sensor 18, to the geolocation data acquisition means 20, to the geolocation data transmission means 22, to the pedometer 23 and to the electrical power supply means 26. The programmable microcontroller 24 is, for example, programmed to periodically transmit a data transmission command signal to the data transmission means 22. For example, the period of transmission of the data transmission command signal can be programmed to be substantially equal to 10 minutes. In a variant, in the preferential exemplary embodiment according to which the first electronic geolocation device 10 comprises a motion sensor 18, the programmable microcontroller 24 is programmed to transmit a data transmission command signal to the data transmission means 22, when a movement of the device 10 is detected by the motion sensor 18. In addition to the electrical energy saving in the electrical power supply means 26 mentioned above, this makes it possible to reduce the number of data transmissions over the network 14 by the electronic device 10, and thus makes it possible to advantageously reduce the consumption of computing resources necessary for the detection of the wearing by the patient 2 of the apparatus 4.

In the exemplary embodiment according to which the first electronic geolocation device 10 comprises a pedometer 23, the data transmitted by the data transmission means 22 comprise, in addition to the geolocation data, the measurement data concerning the number of steps of the patient 2 supplied by the pedometer 23.

The second electronic geolocation device 16 is linked to the data processing equipment item 12 via the communication network 14. The second electronic geolocation device 16 is suitable for being fixed directly to the body of the patient 2, for example on a wrist thereof, as illustrated in FIG. 1. In this case, the second electronic geolocation device 16 for example takes the form of an electronic geolocation bracelet. The electronic bracelet comprises, for example, a GPS tracking beacon, preferably a GPS tracking beacon with instantaneous triggering on movement of the device. The second electronic geolocation device 16 has dimensions compatible with being worn on a limb of the patient, typically a wrist, which is not to be a hindrance for the patient in his or her walking movement. The thickness of the GPS tracking beacon within the second electronic geolocation device 16 is, for example, of the order of a few millimeters.

The second electronic geolocation device 16 comprises components similar to those of the first electronic geolocation device 10. Thus, the second electronic geolocation device 16 comprises electrical power supply means 38, geolocation data acquisition means 32 and means 34 for transmitting geolocation data over the communication network 14, to the data processing equipment item 12. Preferably, as illustrated in FIG. 2, the second electronic geolocation device 16 further comprises a motion sensor 30, a pedometer 35 and a programmable microcontroller 36. In a variant, the programmable microcontroller 36 can be replaced by any type of computation and data processing means, such as, for example, a processor or a microprocessor. The structures and functionalities of the components 30, 32, 34, 35, 36, 38 are identical to those of the counterpart components 18, 20, 22, 23, 24, 26 of the first electronic geolocation device 10, and will not therefore be described in detail. For example, the geolocation data acquisition means 32 are linked to the data transmission means 34 and are configured to periodically trigger an acquisition of data.

The data processing equipment item 12 is suitable, following the reception of geolocation data transmitted by the first geolocation device 10, for detecting a movement of the foot ulcer offloading apparatus 4 and for deducing therefrom the wearing by the patient 2 of the offloading apparatus 4. More specifically, as illustrated in FIG. 2, the data processing equipment item 12 comprises a server 40. The server 40 comprises a processor 42 and a memory 44 linked to the processor 42. The memory stores an application 46 suitable, when it is implemented by the processor 42, for detecting a movement of the foot ulcer offloading apparatus 4 and for deducing therefrom the wearing by the patient 2 of the offloading apparatus 4, following the reception of geolocation data transmitted by the first geolocation device 10. The application 46 is also suitable, when it is implemented by the processor 42, for determining the distance covered by the patient 2 provided with the offloading apparatus 4 or even the period of time the offloading apparatus 4 is worn. In the exemplary embodiment according to which the first electronic geolocation device 10 comprises a pedometer 23, this determination by the application 46 of the distance covered by the patient 2 provided with the offloading apparatus 4 is performed by averaging between a distance estimated from the geolocation data received, and a distance estimated from the measurement data concerning the number of steps of the patient 2.

The server 40 also comprises means 48 for sending messages 50 over the communication network 14, linked to the processor 42.

Preferably, the server 40 is a web server and hosts a web access interface, such an interface not being represented in the figures for reasons of clarity. More preferably, the server 40 of the data processing equipment item 12 is suitable, via the implementation of the application 46 by the processor 42, for periodically generating tables and/or lists tracking the activity of the patient 2, and/or actigraphy-actimetry data relating to the patient 2, and/or comparative data concerning the activity of the patient 2, and/or data indicative of the state of the GPS tracking beacons or of the electrical power supply means 26, 38.

In the particular embodiment illustrated in FIG. 2, the data processing equipment item 12 further comprises a monitoring station 52. The monitoring station 52 comprises, for example, display means and/or means for sending messages over the communication network 14.

In the particular exemplary embodiment of FIGS. 1 and 2 according to which the detection system 1 comprises a second geolocation device 16, the data processing equipment item 12 is suitable, following the reception of the geolocation data transmitted by the second electronic geolocation device 16 and possibly by the first electronic geolocation device 10, for computing an offloading rate associated with the wearing by the patient 2 of the offloading apparatus 4. More specifically, according to this particular exemplary embodiment, the application 46 is suitable, when it is implemented by the processor 42, for computing the offloading rate, following the reception of the geolocation data transmitted by the second device 16 and possibly by the first device 10. The offloading rate associated with the wearing by the patient 2 of the offloading apparatus 4 is defined as the ratio between the period of time during which the patient moves around without the offloading apparatus 4 and the period of time during which he or she moves around with the offloading apparatus 4. The period of time during which the patient moves around with the offloading apparatus 4 can be deduced from the reception of the geolocation data transmitted by the first geolocation device 10, as described above.

The period of time during which the patient moves around without the offloading apparatus 4 can, for example, be deduced from the reception of geolocation data transmitted by the second geolocation device 16 and exhibiting distinct successive values, and from the reception of geolocation data transmitted by the first geolocation device 10 and exhibiting constant successive values, in the exemplary embodiment according to which the first and second geolocation devices 10, 16 do not comprise a motion sensor. In effect, according to this exemplary embodiment, when the patient 2 moves around without the offloading apparatus 4, the second geolocation device 16 transmits geolocation data exhibiting distinct successive values, whereas the first geolocation device 10 transmits geolocation data exhibiting constant successive values. The period of time during which the patient moves around without the offloading apparatus 4 can also be deduced from the reception of the geolocation data transmitted by the second geolocation device 16, and from the non-reception of geolocation data from the first geolocation device 10, in the exemplary embodiment according to which the first and second geolocation devices 10, 16 each comprise a motion sensor 18, 30. In effect, according to this exemplary embodiment, when the patient 2 moves around without the offloading apparatus 4, the second geolocation device 16 transmits geolocation data over the communication network 14, whereas the first geolocation device 10 does not transmit any.

The computation of such an offloading rate is particularly useful to a practitioner following the patient 2. In effect, the practitioner can then advantageously assess the observance of the offloading by his or her patient. In particular, by virtue of the computation of this offloading rate, the practitioner can discriminate between non-observing patients and the patients that correctly observe their treatment but show an unfavorable trend despite correct offloading. The first, who do not always wear their offloading apparatus 4 when they walk, will require reeducation for the correct monitoring of their treatment. The second, who always wear their offloading apparatus 4 when they walk, will require additional therapies. The characteristics relating to the presence of a second geolocation device 16 thus make it possible to further improve the accuracy of the detection and of the determination of the period of time the offloading apparatus is worn by the patient, and to allow a practitioner to refine and improve the therapeutic strategy for managing his or her patients.

The communication network 14 is provided with a private or wide-area communication infrastructure allowing the connection, or access, to communication equipment items of server and/or database and/or electronic communication device type. Conventionally, the communication infrastructure forms a wireless network, or a network comprising a wireless portion and a wired portion. According to a particular exemplary embodiment, the communication network 14 is designed as a cellular network of GSM (Global System for Mobile Communication), or GPRS (General Packet Radio Service) or even UMTS (Universal Mobile Telecommunications System) type. In a variant, the communication network 14 can be designed as a network of Internet type, for example comprising a network portion conforming to the GSM, GPRS or UMTS standard.

Figure 3:
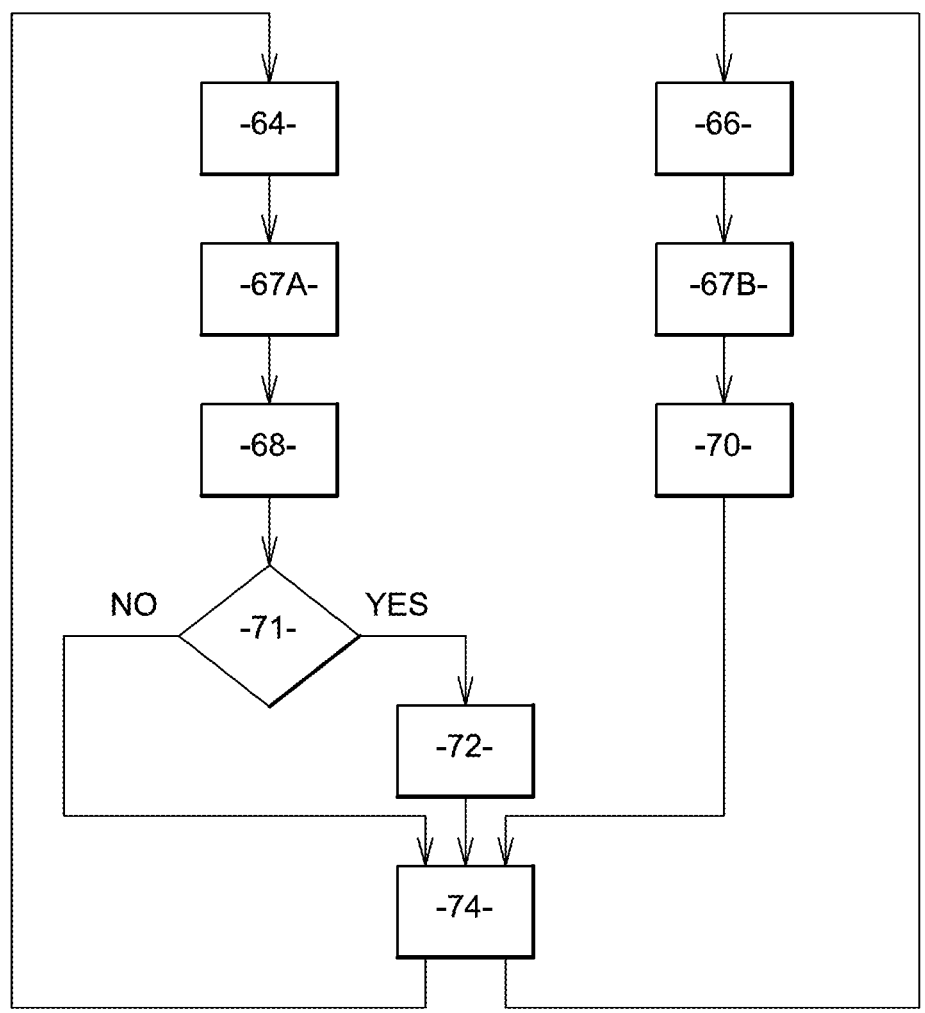
FIG. 3 is a flow diagram representing a method for detecting the wearing by a patient of a foot ulcer offloading apparatus according to the invention, as implemented by the system of FIG. 2.

The method for detecting the wearing by the patient 2 of the offloading apparatus 4 according to the invention, implemented by the detection system 1 of FIG. 2, will now be described with reference to FIG. 3.

During an initial step 64, the means 20 of the first electronic geolocation device 10 acquire geolocation data. This acquisition is performed on a periodic basis, after a loopback of the method, whether or not the patient 2 is wearing the offloading apparatus 4 and has or has not initiated a walking movement.

In the particular exemplary embodiment of FIG. 2 according to which the detection system 1 comprises a second geolocation device 16, during a parallel step 66, the means 32 of the second electronic geolocation device 16 acquire geolocation data. This acquisition is performed on a periodic basis, after a loopback of the method, whether or not the patient 2 is wearing the second geolocation device 16 and has or has not initiated a walking movement.

Preferably, during a step 67A following the step 64, the motion sensor 18 of the first electronic geolocation device 10 detects, if appropriate, a movement of the first device 10, indicating a movement of the patient 2. At the end of this step 67A, the motion sensor 18 delivers, if appropriate, a signal to the programmable microcontroller 24, which itself delivers a transmission command signal to the geolocation data transmission means 22.

In the particular exemplary embodiment of FIG. 2, during a preferential step 67B which follows the step 66, the motion sensor 30 of the second electronic geolocation device 16 detects, if appropriate, a movement of the second device 16, indicating a movement of the patient 2. At the end of this step 67B, the motion sensor 30 delivers, if appropriate, a signal to the programmable microcontroller 36, which itself delivers a transmission command signal to the geolocation data transmission means 34.

During a step 68 following the step 64 or the step 67A, as appropriate, the geolocation data transmission means 22 of the first geolocation device 10 transmit geolocation data acquired by the means 20, over the communication network 14, to the data processing equipment item 12. In the exemplary embodiment according to which the first geolocation device 10 comprises a motion sensor 18, the transmission means 22 transmit the acquired data only if a movement has been detected by the motion sensor 18. In the exemplary embodiment according to which the first electronic geolocation device 10 comprises a pedometer 23, the data transmitted by the data transmission means 22 comprise, in addition to the geolocation data, measurement data concerning the number of steps of the patient 2 supplied by the pedometer 23.

In the particular exemplary embodiment of FIG. 2, during a step 70 following the step 66 or the step 67B, as appropriate, the geolocation data transmission means 34 of the second geolocation device 16 transmit the geolocation data acquired by the means 32, over the communication network 14, to the data processing equipment item 12. In the exemplary embodiment according to which the second geolocation device 16 comprises a motion sensor 30, the transmission means 34 transmit the acquired data only if a movement has been detected by the motion sensor 30. In the exemplary embodiment according to which the second electronic geolocation device 16 comprises a pedometer 35, the data transmitted by the data transmission means 34 comprise, in addition to the geolocation data, the measurement data concerning the number of steps of the patient 2 supplied by the pedometer 35.

During a step 71 following the step 68, the data processing equipment item 12 determines whether it has received, from the first geolocation device 10, geolocation data exhibiting distinct successive values. In a variant, in the exemplary embodiment according to which the first geolocation device 10 comprises a motion sensor 18, the data processing equipment item 12 determines whether it has received geolocation data from the first geolocation device 10. More specifically, during the step 71, the application 46 is implemented by the processor 42 and performs this determination. In all cases, if the response to this determination is no, the method goes on to a subsequent step 74 described herein below.

If the response to this determination is yes, the data processing equipment item 12 detects, during a subsequent step 72, the wearing by the patient 2 of the foot ulcer offloading apparatus 4. More specifically, during the step 72, the application 46, implemented by the processor 42, detects a movement of the offloading apparatus 4 and deduces therefrom the wearing by the patient 2 of the offloading apparatus 4. Advantageously, the application 46, once implemented by the processor 42, determines the distance covered by the patient 2 provided with the offloading apparatus 4 or even the period of time the offloading apparatus 4 is worn. Even more advantageously, the application 46, once implemented by the processor 42, generates tables and/or lists tracking the activity of the patient 2, and/or actigraphy-actimetry data relating to the patient 2, and/or comparative data concerning the activity of the patient 2, and/or data indicative of the state of the GPS tracking beacons or of the electrical power supply means 26, 38. This information generated periodically can advantageously be viewed by a user accessing the web interface of the server 40, via the communication network 14. To do this, the patient 2 can download a specific application to a mobile communication device of smartphone type for example, via the communication network 14. Once this specific application is implemented on his or her mobile communication device, the patient 2 can then access, via the communication network 14, the web interface of the server 40, enabling him or her to view, on his or her device, the information generated periodically by the application 46 of the server 40.

In the particular exemplary embodiment of FIG. 2, during a final step 74 following the step 70 and the step 71 or the step 72, in other words whether or not the data processing equipment item 12 has detected the wearing by the patient 2 of the foot ulcer offloading apparatus 4, the equipment item 12 computes an offloading rate associated with the wearing by the patient 2 of the offloading apparatus 4. More specifically, during the step 74, the application 46 is implemented by the processor 42, and computes the offloading rate, following the reception of the geolocation data transmitted by the second electronic geolocation device 16 and possibly by the first electronic geolocation device 10.

At the end of the final step 74, the method loops back to the initial steps 64, 66.

In a variant, the steps 64, 66, 67A, 67B, 68 and 70 can be interleaved, and not strictly parallel.

In another variant, the detection system 1 does not comprise any second electronic geolocation device 16. In this case, only the steps 64, 67A, 68, 71 and 72 are implemented, the method looping back at the end of the step 72. According to this variant embodiment, the data processing equipment item 12 does not compute any offloading rate.

Advantageously, the server 40 of the data processing equipment item 12 can trigger an alarm if no activity or little activity is detected in the patient 2. In effect, such a situation can be the sign of a loss of consciousness of the patient 2. More specifically, in the preferential exemplary embodiment according to which the first geolocation device 10 comprises a motion sensor 18, the server 40 can trigger an alarm if it receives no geolocation data from the first geolocation device 10 during a predetermined time period. In a variant, in the exemplary embodiment according to which the geolocation device 10 does not comprise any motion sensor, the server 40 can trigger an alarm if the geolocation data received from the first geolocation device 10 during a predetermined time period exhibit constant or quasi-constant values. This alarm can, for example, take the form of the sending of an alarm message 50 to the monitoring station 52 and/or to a mobile communication device 74 of a determined person.

In another variant, when the patient 2 wears a second geolocation device 16, for example in the form of an electronic bracelet, the detection of a non-activity of the patient 2 leading to the triggering of an alarm can correspond to a non-reception of data from the first geolocation device 10 during a predetermined time period, correlated with a non-reception of data from the second geolocation device 16 during this same time period.

It should be noted that this alarm can take several forms. It can take the form of a display on a screen in a monitoring room and/or the sending of a message to a determined person, for example via a mobile communication device 74 belonging to that person. This sending to a determined person can be performed directly by the server 40 via the sending of a message 50 over the communication network 14, or indirectly via the monitoring station 52 after having previously received an alarm message 50.

Figure 4:
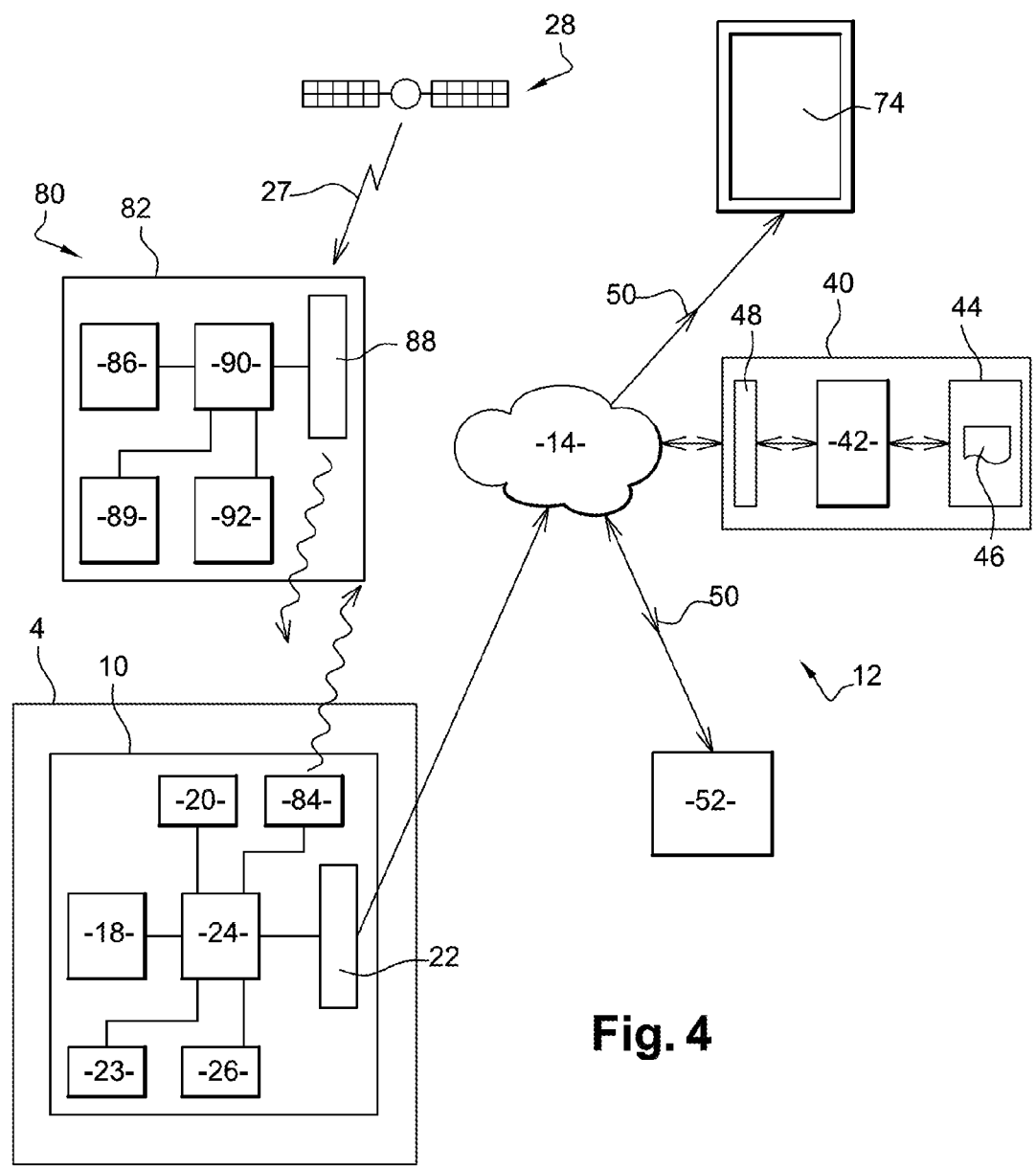
FIG. 4 is a view similar to that of FIG. 2 of a system for detecting the wearing by a patient of a foot ulcer offloading apparatus according to a second embodiment.

FIG. 4 illustrates a system 80 for detecting the wearing by a patient 2 of a foot ulcer offloading apparatus 4, according to a second embodiment of the invention for which the elements similar to the first embodiment, described previously in light of FIGS. 1 and 2, are identified by identical references, and are therefore not described again.

In this second embodiment, the detection system 80 comprises, in addition to the data processing equipment item 12, an electronic geolocation device 10 and an electronic communication device 82.

In this second embodiment, the electronic geolocation device 10 further comprises a radiofrequency signal transceiver 84. The transceiver 84 is linked to the programmable microcontroller 24. The transceiver 84 is, for example, a short-range radiofrequency signal transceiver. The transceiver 84 is, for example, a transceiver conforming to the Bluetooth standard.

Furthermore, in this second embodiment, the programmable microcontroller 24 is suitable for determining whether a radiofrequency link has been established between the transceiver 84 and the electronic communication device 82. The microcontroller 24 is suitable for determining that a radiofrequency link has been established with the electronic communication device 82, if it first receives a radiofrequency signal transmitted by the electronic communication device 82, following the establishment of a predetermined communication protocol between the geolocation device 10 and the electronic communication device 82. The programmable microcontroller 24 is programmed to transmit a data transmission command signal to the data transmission means 22, accompanied by a first notification if a radiofrequency link has been established between the transceiver 84 and the electronic communication device 82; and to transmit a data transmission command signal to the data transmission means 22, accompanied by a second notification if no radiofrequency link has been established with the electronic communication device 82.

The first notification is a notification indicating the presence of a radiofrequency coupling between the geolocation device 10 and the electronic communication device 82, via the established radiofrequency link. The second notification is a notification indicating the absence of radiofrequency coupling between the geolocation device 10 and the electronic communication device 82.

The electronic communication device 82 is suitable for being fixed directly to the body of the patient 2, for example on a wrist thereof. In this case, the electronic communication device 82 for example takes the form of an electronic radiofrequency signal communication bracelet. The electronic bracelet comprises, for example, a short-range radiofrequency signal communication beacon. The electronic communication device 82 has dimensions compatible with being worn on a limb of the patient, typically a wrist, which is not to hamper the patient in his or her walking movement.

The electronic communication device 82 comprises electrical power supply means 92 and a radiofrequency signal transceiver 88. Preferably, as illustrated in FIG. 4, the second electronic communication device 82 further comprises a motion sensor 86, a pedometer 89 and a programmable microcontroller 90. In a variant, the programmable microcontroller 90 can be replaced by any type of computation and data processing means, such as, for example, a processor or a microprocessor.

The electrical power supply means 92 are, for example, able to supply a nominal electrical voltage substantially equal to 12 V. The electrical power supply means 92 are, for example, formed by a lithium battery. The electrical power supply means 92 are, for example, able to provide the electronic communication device 82 with electrical autonomy of the order of several months.

The transceiver 88 is, for example, a short-range radiofrequency signal transceiver. The transceiver 88 is, for example, a transceiver conforming to the Bluetooth standard.

The motion sensor 86 is linked to the transceiver 88. In the exemplary embodiment of FIG. 4, the motion sensor 86 is connected to the programmable microcontroller 90, the latter being also connected to the radiofrequency signal transceiver 88. The motion sensor 86 is, for example, a triaxial linear accelerometer, capable of delivering a signal as soon as a non-zero acceleration value is measured. In a variant, the motion sensor 86 is an instantaneous speed sensor. In the exemplary embodiment according to which the electronic communication device 82 comprises a motion sensor 86, the transceiver 88 is configured to transmit radiofrequency signals when a movement of the communication device 82 is detected by the motion sensor 86. This exemplary embodiment advantageously makes it possible to save electrical energy in the electrical power supply means 92, the transceiver 88 not transmitting radiofrequency signals on a periodic basis but only if a movement of the communication device 82 has been detected by the motion sensor 86.

The pedometer 89 is connected to the programmable microcontroller 90 and is able to supply measurement data concerning the number of steps of the patient 2.

The programmable microcontroller 90 is linked to the motion sensor 86, to the transceiver 88, to the pedometer 89 and to the electrical power supply means 92. The programmable microcontroller 90 is, for example, programmed to periodically transmit a radiofrequency signal transmission command signal to the transceiver 88. In a variant, in the exemplary embodiment according to which the communication device 82 comprises a motion sensor 86, the programmable microcontroller 90 is programmed to transmit a radiofrequency signal transmission command signal to the transceiver 88, when a movement of the electronic communication device 82 is detected by the motion sensor 86.

In the particular embodiment of FIG. 4 according to which the detection system 80 comprises a communication device 82, there is no longer any transmission of data by a second geolocation device over the communication network 14. Consequently, the detection system 80 according to the second embodiment of the invention advantageously makes it possible to reduce the volume of geolocation data transmitted, and reduce the bandwidth consumption. Furthermore, this detection system 80 according to the second embodiment advantageously allows a practitioner tracking the patient 2 to determine whether the patient is correctly wearing the elements for detecting the wearing of the offloading apparatus, consisting of the geolocation device 10 and the communication device 82. In effect, the case where the geolocation device 10 does not comprise a motion sensor is considered, the conclusion being able to be transposed likewise to the case where the geolocation device 10 comprises a motion sensor 18. If the practitioner accesses the data processing equipment item 12 and the latter receives, from the electronic geolocation device 10, geolocation data exhibiting constant successive values, several possibilities can be considered:

the patient 2 is wearing the geolocation device 10 and the communication device 82, and is immobile;

the patient 2 is wearing the communication device 82 but is not wearing the offloading apparatus 4 provided with the geolocation device 10, and the patient 2 is walking.

Now, the information on radiofrequency coupling or not between the geolocation device 10 and the electronic communication device 82, which is reflected by the presence of a first or of a second notification accompanying the geolocation data transmitted, is received by the data processing equipment item 12. The reception of this information thus allows the practitioner accessing the equipment item 12 to be able to discriminate between these two situations and thus obtain more accurate information as to the observance of the offloading by his or her patient. Furthermore, the situation according to which the patient 2 is wearing the offloading apparatus 4 provided with the geolocation device 10 but is not wearing the communication device 82, and according to which the patient 2 is walking, can advantageously be detected by the data processing equipment item 12. In effect, this situation corresponds to a reception of geolocation data exhibiting distinct successive values accompanied by a second notification indicative of the absence of radiofrequency coupling between the geolocation device 10 and the electronic communication device 82. Thus, in this second embodiment of the invention, the data processing equipment item 12 is also suitable, following the reception of the geolocation data transmitted by the geolocation device 10, accompanied by the first or the second notification, for computing the offloading rate associated with the wearing by the patient 2 of the offloading apparatus 4. The accuracy of the detection and of the determination of the period of time the offloading apparatus is worn by the patient are thus advantageously improved.

In operation, the method for detecting the wearing by the patient 2 of the offloading apparatus 4 according to the invention, implemented by the detection system 80 of FIG. 4, proceeds as follows.

During an initial step, the means 20 of the electronic geolocation device 10 acquire geolocation data. This acquisition is performed on a periodic basis, after a loopback of the method, whether or not the patient 2 is wearing the offloading apparatus 4 and has or has not initiated a walking movement.

Preferably, during a subsequent step, the motion sensor 18 of the electronic geolocation device 10 detects, if appropriate, a movement of the device 10, indicating a movement of the patient 2. At the end of this step, the motion sensor 18 delivers, if appropriate, a signal to the programmable microcontroller 24, which itself delivers a transmission command signal to the geolocation data transmission means 22.

During a parallel or subsequent step, the programmable microcontroller 24 determines whether a radiofrequency link has been established between the transceiver 84 of the geolocation device 10 and the transceiver 88 of the electronic communication device 82. Based on this determination, the programmable microcontroller 24 generates the first or the second notification.

During a subsequent step, the geolocation data transmission means 22 of the geolocation device 10 transmit the geolocation data acquired by the means 20 over the communication network 14, to the data processing equipment item 12, accompanied by the first or the second notification. In the exemplary embodiment according to which the geolocation device 10 comprises a motion sensor 18, the transmission means 22 transmit the acquired data only if a movement has been detected by the motion sensor 18. In the exemplary embodiment according to which the electronic geolocation device 10 and/or the electronic communication device 82 comprises a pedometer 23, 89, the data transmitted by the data transmission means 22 comprise, in addition to the geolocation data, the measurement data concerning the number of steps of the patient 2 supplied by the pedometer 23, 89.

During a subsequent step, the data processing equipment item 12 determines whether it has received, from the geolocation device 10, geolocation data exhibiting distinct successive values. In a variant, in the exemplary embodiment according to which the geolocation device 10 comprises a motion sensor 18, the data processing equipment item 12 determines whether it has received geolocation data from the geolocation device 10. More specifically, during this step, the application 46 is implemented by the processor 42 and performs this determination. In all cases, if the response to this determination is no, the method goes on to a final step described herein below.

If the response to this determination is yes, the data processing equipment item 12 detects, during a subsequent step, the wearing by the patient 2 of the foot ulcer offloading apparatus 4. More specifically, during this step, the application 46, implemented by the processor 42, detects a movement of the offloading apparatus 4 and deduces therefrom the wearing by the patient 2 of the offloading apparatus 4. Advantageously, the application 46, once implemented by the processor 42, determines the distance covered by the patient 2 provided with the offloading apparatus 4 or even the period of time the offloading apparatus 4 is worn. Even more advantageously, the application 46, once implemented by the processor 42, generates tables and/or lists tracking the activity of the patient 2, and/or actigraphy-actimetry data relating to the patient 2, and/or comparative data concerning the activity of the patient 2, and/or data indicative of the state of the GPS tracking beacons or of the electrical power supply means 26.

During a subsequent final step, in other words whether or not the data processing equipment item 12 has detected the wearing by the patient 2 of the foot ulcer offloading apparatus 4, the equipment item 12 computes an offloading rate associated with the wearing by the patient 2 of the offloading apparatus 4. More specifically, during this final step, the application 46 is implemented by the processor 42, and computes the offloading rate, following the reception or non-reception of the geolocation data transmitted by the electronic geolocation device 10, accompanied, as appropriate, by the first or the second notification.

At the end of the final step, the method loops back to the initial step.

A third embodiment of a system for detecting the wearing by a patient 2 of a foot ulcer offloading apparatus 4, not represented in the figures, can consist of a combination of the first and second embodiments represented in FIGS. 2 and 4 respectively. More specifically, according to this third embodiment of the invention, the detection system comprises, in addition to the data processing equipment item 12, a first electronic geolocation device 10, a second electronic geolocation device 16 and an electronic communication device 82. Preferably, the second electronic geolocation device 16 and the electronic communication device 82 are arranged in one and the same casing, typically an electronic bracelet, the dimensions of which are compatible with being worn on a limb of the patient, for example a wrist.

Since the operation of the detection system according to this third embodiment is similar to the operation of the detection system 1 according to the first embodiment, combined with the operation of the detection system 80 according to the second embodiment, the former will not be described in more detail.

The system for detecting the wearing by a patient of a foot ulcer offloading apparatus according to the invention offers several advantages:

to operate, the system requires no connection to a wireless local area network WLAN in the home of the patient;

the system advantageously allows for operation both indoors and outdoors;

the transmission to the data processing equipment item of the geolocation data by the first geolocation device, and by the second geolocation device, is performed automatically with no action on the part of the patient;

the system advantageously allows a patient to be able to view his or her data and his or her offloading times via the connection to the communication network of a mobile communication device of the patient.

The invention has been described with reference to a system for detecting the wearing by a patient of a foot ulcer offloading apparatus. Although just one offloading apparatus is represented in FIGS. 1 and 2, it is understood that the detection system applies in the same way if the patient wears two offloading apparatuses, the system according to the invention making it possible to detect the wearing of each of the offloading apparatuses. Similarly, the detection system according to the invention applies in the same way to a set of patients each wearing one or more foot ulcer offloading apparatuses, the detection system in this case comprising several electronic geolocation devices 10, each geolocation device 10 being suitable for being secured to an offloading apparatus. In this latter case, the data processing equipment item of the detection system according to the invention is suitable for periodically generating tables and/or lists tracking several offloading apparatuses, therefore several patients.

In the claims, the word "comprising" does not exclude other elements.

The invention claimed is:

1. A system for detecting the wearing by a patient of a foot ulcer offloading apparatus comprising:
    an electronic geolocation device secured to the offloading apparatus, wherein the electronic geolocation device comprises:
        an electrical power supply; and
        a geolocation data acquisition device; and
    a data processing equipment item linked to the electronic geolocation device via a communication network;
    electronic communication device fixed directly to a body of the patient, the electronic communication device comprising an electrical power supply and a radiofrequency signal transceiver;
    wherein the electronic geolocation device further comprises:
        a transmitter for transmitting geolocation data over the communication network to the data processing equipment item, the transmitter being linked to the geolocation data acquisition device,
        a programmable microcontroller linked to the transmitter; and
        a radiofrequency signal transceiver linked to the programmable microcontroller, the microcontroller being programmed to transmit a geolocation data transmission command signal to the transmitter, accompanied by a first notification if a radiofrequency link has been established between the transceiver and the electronic communication device; and to transmit a geolocation data transmission command signal to the transmitter, accompanied by a second notification, different from the first notification, if no radiofrequency link has been established between the transceiver and the electronic communication device; and
    wherein the data processing equipment item, following reception of geolocation data transmitted by the electronic geolocation device, detects movement of the foot ulcer offloading apparatus to deduce the wearing by the patient of the foot ulcer offloading apparatus; and
    wherein the data processing equipment item, following the reception of the geolocation data transmitted by the electronic geolocation device and of the first or the second notification, computes an offloading rate associated with the wearing by the patient of the foot ulcer offloading apparatus.

2. The system as claimed in claim 1, wherein the electronic geolocation device further comprises a motion sensor linked to the transmitter, the transmitter being configured to transmit geolocation data to the data processing equipment item when a movement of the device is detected by the motion sensor.

3. The system as claimed in claim 1, further comprising a second electronic geolocation device suitable for being fixed directly to the body of the patient, the second geolocation device being linked to the data processing equipment item via the communication network and comprising a second electrical power supply, second geolocation data acquisition device and second transmitter for transmitting geolocation data over the communication network to the data processing equipment item, the second transmitter being linked to the second acquisition device.

4. The system as claimed in claim 3, in which the second electronic geolocation device further comprises a second motion sensor linked to the second transmitter, the second transmitter being configured to transmit geolocation data to the data processing equipment item when a movement of the device is detected by the second motion sensor.

5. The system as claimed in claim 2, further comprising a second electronic geolocation device suitable for being fixed directly to the body of the patient, the second geolocation device being linked to the data processing equipment item via the communication network and comprising a second electrical power supply, second geolocation data acquisition device and second transmitter for transmitting geolocation data over the communication network to the data processing equipment item, the second transmitter being linked to the second acquisition device.

6. The system as claimed in claim 5, in which the second electronic geolocation device further comprises a second motion sensor linked to the second transmitter, the second transmitter being configured to transmit geolocation data to the data processing equipment item when a movement of the device is detected by the second motion sensor.

7. The system as claimed in claim 4, in which at least one of the first or second geolocation devices comprises a GPS tracking beacon triggered instantaneously on movement of the device.

8. The system as claimed in claim 3, wherein the data processing equipment item, following the reception of the geolocation data transmitted by the electronic geolocation devices, computes an offloading rate associated with the wearing by the patient of the foot ulcer offloading apparatus.

9. The system as claimed in claim 1, wherein the electronic communication device further comprises a motion sensor linked to the radiofrequency signal transceiver, the transceiver configured to transmit radiofrequency signals when a movement of the communication device is detected by the motion sensor.

10. The system as claimed in claim 1, wherein the data processing equipment item comprises a server that includes a processor and a memory linked to the processor, the memory storing an application, when implemented by the processor, to detect the movement of the foot ulcer offloading apparatus and to deduce the wearing by the patient of the offloading apparatus, following the reception of the geolocation data transmitted by the electronic geolocation device.

11. A method for detecting the wearing by a patient of a foot ulcer offloading apparatus, the method being implemented by a detection system comprising;
    an electronic geolocation device comprising:
    an electrical power supply;
    a geolocation data acquisition device; and
    a data processing equipment item linked to the electronic geolocation device via a communication network, the electronic geolocation device being secured to a foot ulcer offloading apparatus and further comprising a transmitter for transmitting geolocation data over the communication network to the data processing equipment item, the transmitter being linked to the acquisition device, the method comprising:
    steps: acquiring geolocation data by the data acquisition device; transmitting the acquired geolocation data over the communication network, to the data processing equipment item;
    detecting by the data processing equipment item, from the received geolocation data, a movement of the foot ulcer offloading apparatus, and, consequently, of the wearing by the patient of the foot ulcer offloading apparatus; and
    computing an offloading rate associated with the wearing by the patient of the foot ulcer offloading apparatus.

12. A method for detecting the wearing by a patient of a foot ulcer offloading apparatus, the method being implemented by a detection system comprising:
- an electronic geolocation device comprising:
  - an electrical power supply;
  - a geolocation data acquisition device; and
- a data processing equipment item linked to the electronic geolocation device via a communication network, the electronic geolocation device being secured to a foot ulcer offloading apparatus and further comprising a transmitter for transmitting geolocation data over the communication network to the data processing equipment item, the transmitter being linked to the acquisition device,
- an electronic communication device fixed directly to a body of the patient, and comprising an electrical power supply and a radiofrequency signal transceiver;
- the electronic geolocation device further comprises:
  - a programmable microcontroller linked to the transmitter; and
  - a radiofrequency signal transceiver linked to the programmable microcontroller, the method comprising:
- acquiring geolocation data by the data acquisition device;
- transmitting the acquired geolocation data over the communication network, to the data processing equipment item;
- detecting by the data processing equipment item, from the received geolocation data, a movement of the foot ulcer offloading apparatus, and, consequently, of the wearing by the patient of the offloading apparatus;
- determining, by the programmable microcontroller, whether a radiofrequency link has been established between the transceiver of the electronic geolocation device and the transceiver of the electronic communication device;
- transmitting, by the programmable microcontroller, of a geolocation data transmission command signal to the transmitter, accompanied by a first notification if a radiofrequency link has been established between the electronic geolocation device and the electronic communication device; or by a second notification, different from the first notification, if no radiofrequency link has been established between the electronic geolocation device and the electronic communication device; and
- computing, by the data processing equipment item, of an offloading rate associated with the wearing by the patient of the foot ulcer offloading apparatus whether or not the data processing equipment item has detected the wearing by the patient of the foot ulcer offloading apparatus;
- wherein, in the transmitting of the acquired geolocation data, the transmitted geolocation data are accompanied by the first or the second notification.

* * * * *